United States Patent [19]
Kudo et al.

[11] Patent Number: 5,095,907
[45] Date of Patent: Mar. 17, 1992

[54] ACOUSTIC WAVE THERAPY APPARATUS

[75] Inventors: Nobuki Kudo; Satoshi Nomura, both of Tochigi, Japan

[73] Assignee: Kabushiki Kaisha Toshiba, Kawasaki, Japan

[21] Appl. No.: 540,497

[22] Filed: Jun. 19, 1990

[30] Foreign Application Priority Data

Jun. 21, 1989 [JP] Japan .................. 1-158804

[51] Int. Cl.$^5$ .................. A61B 17/22; A61B 8/00
[52] U.S. Cl. .................. 128/660.03; 128/804; 128/24 EL
[58] Field of Search ............. 128/24 EL, 660.03, 804; 606/127–128

[56] References Cited

U.S. PATENT DOCUMENTS

| | | | |
|---|---|---|---|
| 2,559,227 | 7/1951 | Rieber | 129/24 |
| 4,532,939 | 8/1985 | Yuki | 128/804 |
| 4,646,756 | 3/1987 | Watmough et al. | 128/804 |
| 4,669,483 | 6/1987 | Hepp et al. | 128/660 |
| 4,771,787 | 9/1988 | Worster et al. | 128/24 EL |
| 4,821,724 | 4/1989 | Makofski et al. | 128/24 EL |
| 4,858,613 | 8/1989 | Fry et al. | 128/660.03 |
| 4,928,672 | 5/1990 | Grasser et al. | 128/24 |
| 4,962,754 | 10/1990 | Okazaki | 128/660.03 |

FOREIGN PATENT DOCUMENTS

| | | | |
|---|---|---|---|
| 0206331 | 12/1986 | European Pat. Off. | 128/24 EL |
| 0265741 | 5/1988 | European Pat. Off. | 128/24 EL |
| 0316863 | 5/1989 | European Pat. Off. | 128/24 EL |
| 8716496.5 | 5/1989 | Fed. Rep. of Germany . | |
| 87/03797 | 7/1987 | World Int. Prop. O. . | |

Primary Examiner—Ruth S. Smith
Attorney, Agent, or Firm—Foley & Lardner

[57] ABSTRACT

In an acoustic wave therapy apparatus, a holder is provided with an irradiation device for generating acoustic waves for medical treatment, and a bag having a variable size and containing an acoustic wave propagation medium. The holder is also provided with a probe rod having at its one end an ultrasonic probe for ultrasonic tomographic imaging. The probe rod has at least one opening at its one end. A pipe is connected to the opening of the probe rod. The pipe is connected to fluid equipment for supplying and discharging the acoustic wave propagation medium into and from the bag member. The holder is held by a hand-type holding apparatus. A connector for connecting and disconnecting the pipe is arranged on a C-arm included in the hand-type holding apparatus.

23 Claims, 11 Drawing Sheets

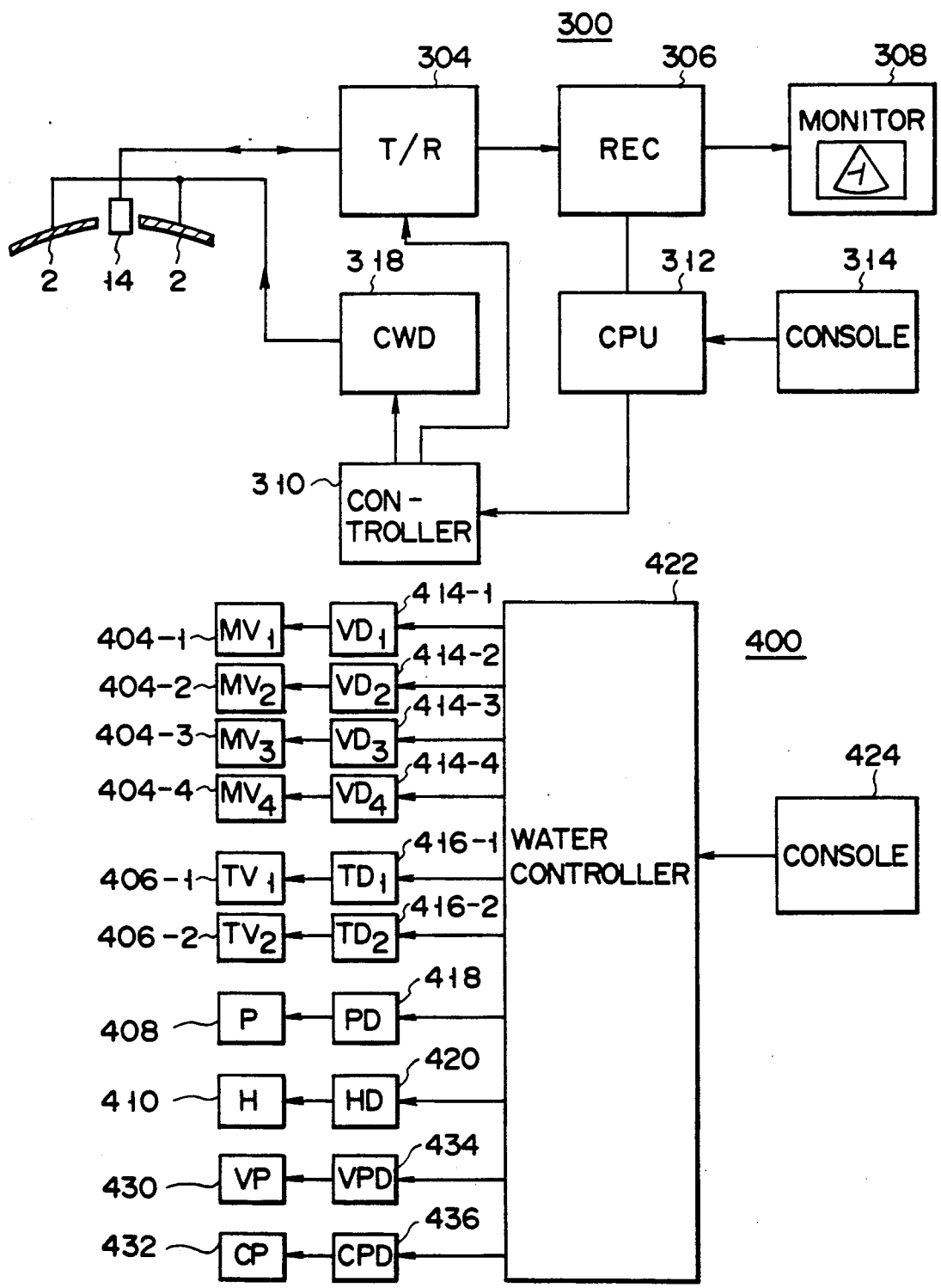
F I G. 11

ACOUSTIC WAVE THERAPY APPARATUS

BACKGROUND OF THE INVENTION

1. Field of the Invention

The present invention relates generally to an acoustic wave therapy apparatus for treating cancerous cells or calculi in a human body, using shock waves produced by acoustic waves or continuous acoustic waves, and more particularly to an ultrasonic shock wave lithotrity apparatus and an ultrasonic continuous wave hyperthermic therapy apparatus.

2. Description of the Related Art

Conventional acoustic wave treatment apparatuses include an ultrasonic shock wave lithotrity apparatus for breaking calculi, etc. in a human body, using shock waves due to focusing ultrasonic energy, and an ultrasonic continuous wave hyperthermic therapy apparatus for treating a tumor by heating it up to a lethal temperature, using continuous focusing ultrasonic energy.

This type of acoustic wave treatment apparatus generally has an irradiation device for generating ultrasonic waves. The irradiation device has a concave surface for focusing the generated ultrasonic waves. The acoustic wave generator is arranged to face a subject, with a bag interposed therebetween. An ultrasonic imaging probe is arranged within the bag, for positioning the irradiation device and for obtaining tomograms of the subject for confirming the result of treatment.

If a large-diameter acoustic wave generator is employed in this apparatus and generated waves are focused onto a region-of-interest (ROI), a maximum treatment effect is attained with a small treatment energy. In this case, however, if the focus of waves departs from the ROI, a normal tissue is damaged. It is thus important to precisely focus the waves onto the ROI.

FIG. 1 is a cross-sectional view for schematically showing a structure of an applicator serving as an important part of an acoustic wave therapy apparatus having this type of imaging means. In FIG. 1, ultrasonic transducers 2 serving as an irradiation device are secured to a holder 4 having a concave surface. The ultrasonic transducers 2 are arranged symmetrical in respect of a probe rod 16 (described later) so that the focal points of the transducers 2 may be positioned at a region-of-interest (ROI) 6.

The acoustic wave therapy apparatus has a bag 10 containing water 8 which is put in close contact with a patient 12. The probe rod 16 having an ultrasonic probe 14 is arranged at the center of the holder 4. The ultrasonic probe 14 effects positioning for treatment by means of an image display process, thereby confirming if the ROI 6 has been treated appropriately In FIG. 1, a dot-and-dash line indicates a region 18 where ultrasonic waves for treatment are radiated, and a two-dot-and-dash line indicates a region 20 (a tomogram display region) where ultrasonic waves for ultrasonic imaging are radiated.

When an acoustic wave therapy is performed by this apparatus, a tomogram is formed on the basis of a reflected wave signal received by the ultrasonic probe 14. Observing the tomograms, an operator moves the apparatus so that the focal points of the ultrasonic transducers 2 may coincide with the location of the ROI 6, or positions the apparatus by supplying water 8 into and letting water 8 out of the bag 10. When the focal points of the transducers 2 have coincided with the location of the ROI 6, the transducers 2 are driven, e.g. by intense pulse waves to radiate intense ultrasonic waves onto the ROI 6, thereby subjecting the ROI 6 to, e.g. lithotrity.

The positioning of the focal points of the transducers 2 relative to the ROI 6 will now be described. The size of the bag 10 is adjusted by supplying the water 8 thereinto and letting out the water 8 therefrom. Thus, the focal points of the transducers 2 can be freely positioned relative to the ROI 6. The water 8 is supplied into and discharged from the bag 10 through a pipe (not shown) arranged above the holder 4 or the bag 10.

In the above apparatus, however, the water 8 in the bag 10 cannot completely be discharged from the bag 10 since the water 8 is discharged through the pipe arranged above the holder 4 or the bag 10. As a result, the water 8 would remain on the bottom of the bag 10, and the ultrasonic probe 14 is always put in the water 8. This leads to deterioration of characteristics of the ultrasonic probe 14.

SUMMARY OF THE INVENTION

The object of the present invention is to provide an acoustic wave therapy apparatus capable of exactly treating a region-of-interest, without deteriorating the characteristics of an ultrasonic probe.

According to one aspect of this invention, there is provided an acoustic wave therapy apparatus comprising:

a holder having a concave surface at least on one side thereof, and also having a through-hole;

acoustic wave generating means, provided on one side of said holder, for generating acoustic waves for medical treatment;

a bag member arranged on said one side of the holder and designed to be put in contact with the surface of a subject, and containing an acoustic wave propagation medium, the size of said bag member being variable;

a rod member inserted into said through-hole of the holder and arranged vertically movable in said bag member; and an ultrasonic probe for ultrasonic wave tomographic imaging, provided at the bag member-side end portion of the rod member, characterized in that said rod member has at least one opening at its one end, a pipe is connected to the opening, and there is provided supply/discharge means for supplying/discharging the acoustic wave propagation medium into/from said bag member through said pipe.

According to another aspect of the invention, there is provided an acoustic wave therapy apparatus comprising:

a holder having a concave surface at least on one side thereof, and also having a through-hole;

acoustic wave generating means, provided on one side of said holder, for generating acoustic waves for medical treatment;

a bag member arranged on said one side of the holder and designed to be put in contact with the surface of a subject, and containing an acoustic wave propagation medium, the size of said bag member being variable;

a rod member inserted into said through-hole of the holder and arranged vertically movable in said bag member; and an ultrasonic probe for ultrasonic wave tomographic imaging, provided at the bag member-side end portion of the rod member, characterized in that said rod member has a plurality of openings at its one end, a plurality of pipes are connected to the openings, and there is provided supply-/discharge means for supplying/discharging the acoustic wave propagation medium into/from said bag member through the pipes.

According to still another aspect of the invention, there is provided an acoustic wave therapy apparatus comprising:

a holder having a concave surface at least on one side thereof, and also having a through-hole;

acoustic wave generating means, provided on one side of said holder, for generating acoustic waves for medical treatment;

a bag member arranged on said one side of the holder and designed to be put in contact with the surface of a subject, and containing an acoustic wave propagation medium, the size of said bag member being variable;

a rod member inserted into said through-hole of the holder and arranged vertically movable in said bag member; and an ultrasonic probe for ultrasonic wave tomographic imaging, provided at the bag member-side end portion of the rod member, characterized in that said rod member has at least one opening at its one end, a pipe is connected to the opening, and there is provided fluid equipment connected to said pipe for supplying/discharging the acoustic wave propagation medium into/from said bag member, said holder is held by a hand-type holding apparatus, and said hand-type holding apparatus comprises a base set on the floor, a column vertically arranged on the base, a C-arm mounted slidably on the column, and a holding mechanism provided on the C-arm for holding the holder, and a connector is provided on the C-arm, for connecting/disconnecting at least said pipe.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 8A to 8C show operation modes of water equipment, in which FIG. 8A illustrates a water supply mode, FIG. 8B a water circulation mode, and FIG. 8C a water discharge mode;

FIGS. 9A and 9B show an applicator and a tomogram in the case where the bag member of the applicator has been contracted by the discharge operation of the water equipment, in which FIG. 9A is a cross-sectional view illustrating the relationship between the applicator and the patient, and FIG. 9B shows a tomogram displayed on a monitor;

FIGS. 10A and 10B show an applicator and a tomogram in the case where the bag member of the applicator has been swelled by the supply operation of the water equipment, in which FIG. 10A is a cross-sectional view illustrating the relationship between the applicator and the patient, and FIG. 10B shows a tomogram displayed on a monitor;

FIG. 11 is a block diagram showing an electric circuit in the case where the embodiment shown in FIG. 2 has been applied to an ultrasonic continuous wave hyperthermic therapy apparatus;

DETAILED DESCRIPTION OF THE PREFERRED EMBODIMENTS

The structure of an acoustic wave therapy apparatus according an embodiment of the present invention will now be described with reference to accompanying FIGS. 2 to 7.

Figure 1:
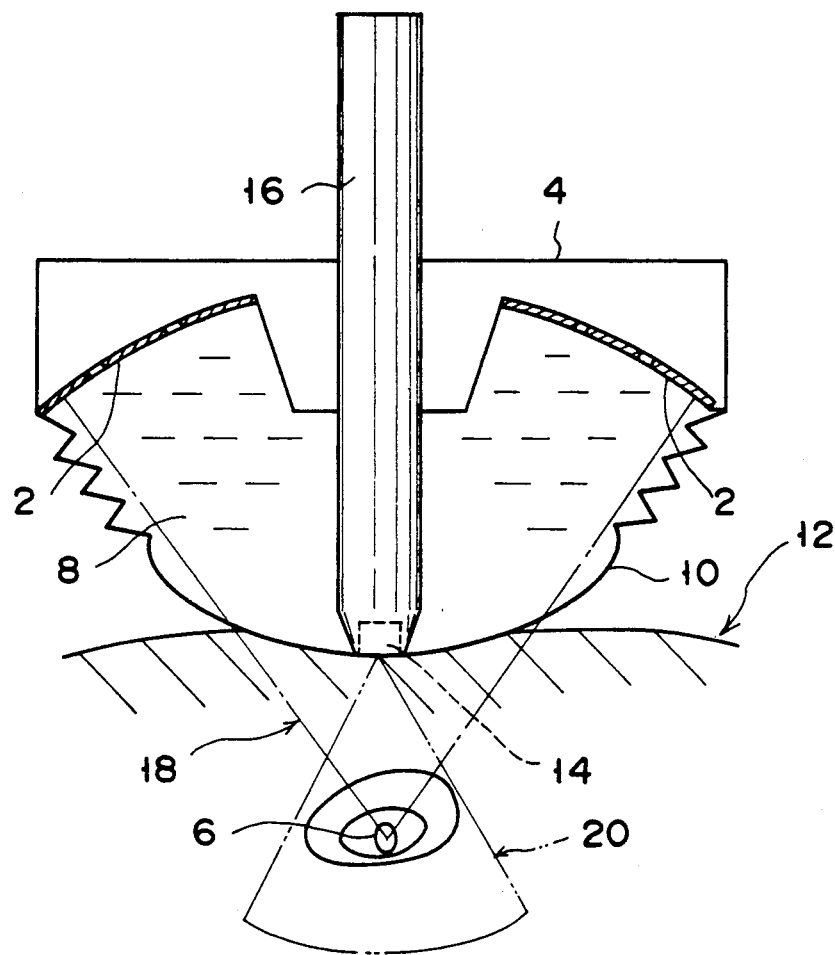
FIG. 1 is a cross-sectional view schematically showing an example of an important portion of a conventional acoustic wave therapy apparatus.
Figure 2:
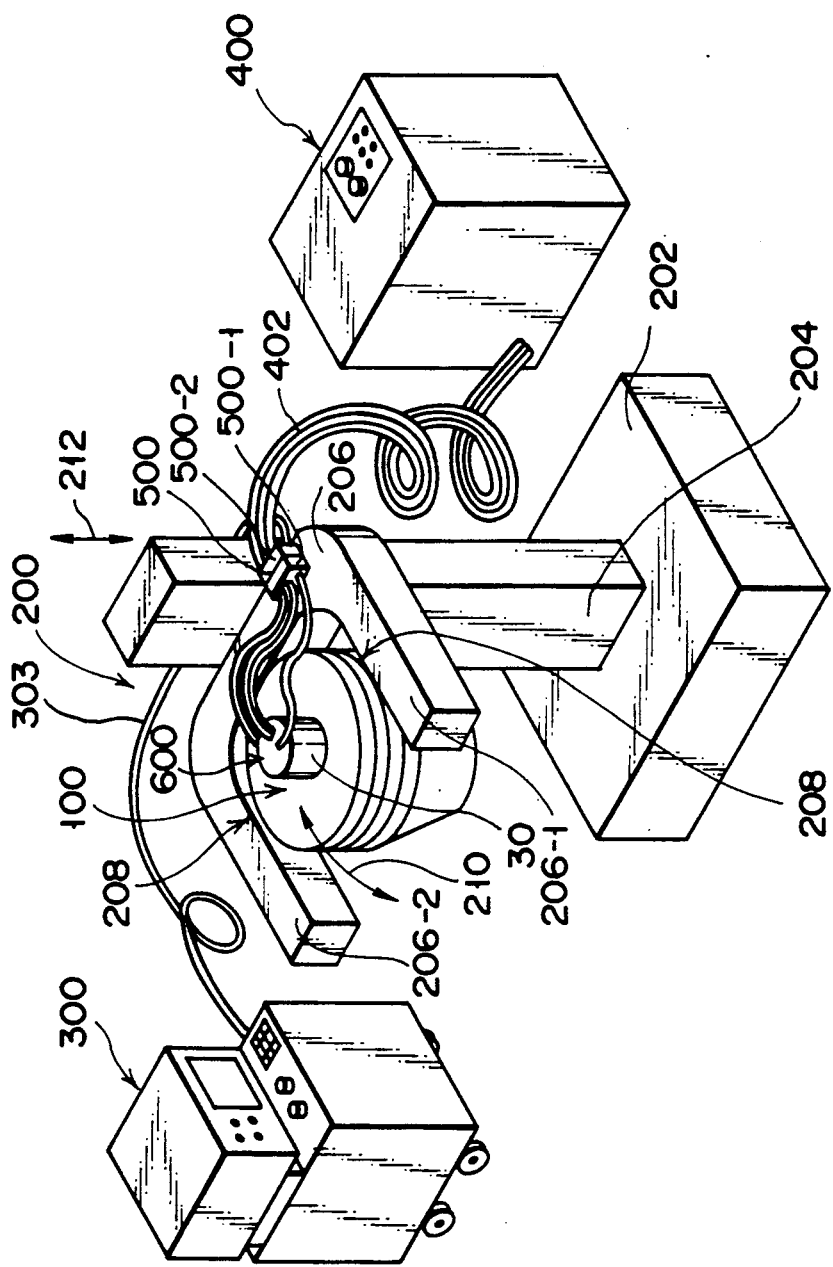
FIG. 2 is a perspective view showing an overall structure of an acoustic wave therapy apparatus according to an embodiment of the present invention.
Figure 3:
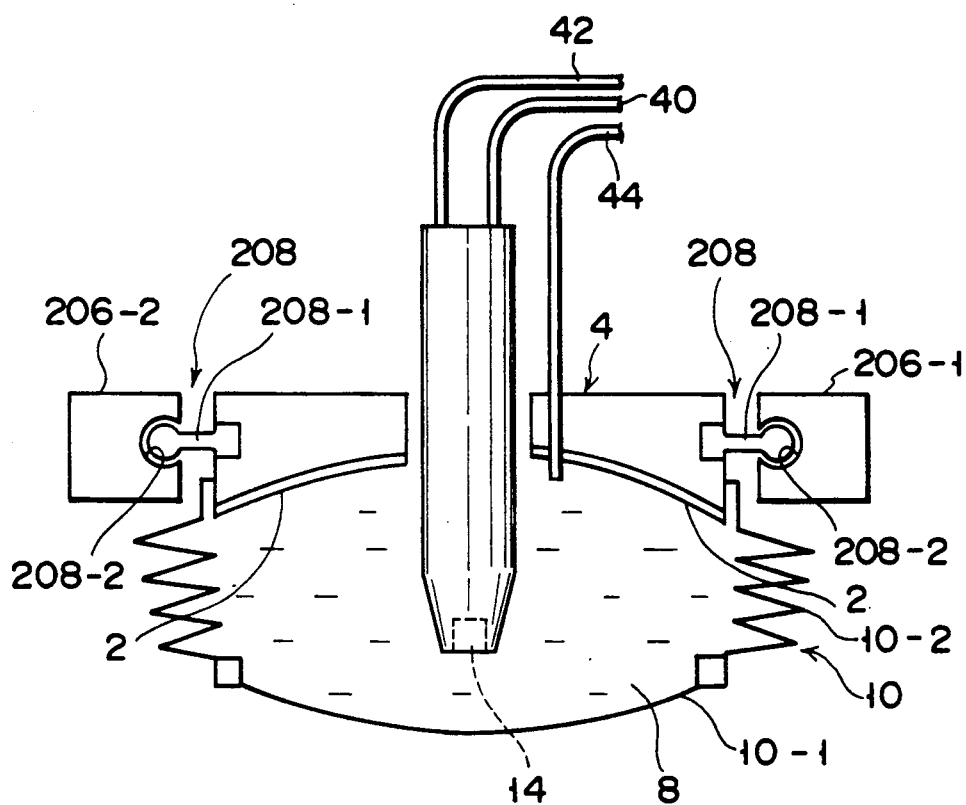
FIG. 3 is a cross-sectional view schematically showing the state of connection between an applicator and a C-arm in the embodiment shown in FIG. 2, wherein pipes, etc. are omitted.

Referring to FIGS. 2 and 3, the overall structure of the apparatus will be described. A holder 4, which is a part of an applicator 100, is held by a hand-type holding apparatus 200. The hand-type holding apparatus 200 comprises a base 202 set on the floor and provided, desirably, with casters, a column 204 vertically arranged on the base 202, a C-arm 206 mounted slidably on the column 204, and a holding mechanism provided on the C-arm 206 for holding the holder 4. The holding mechanism 208 comprises, for example, a ball and socket joint mechanism. As is shown in FIGS. 2 and 3, ball members 208-1 are provided on both side portions 4-1 and 4-2 of the holder 4, socket members 208-2 are provided on mutually facing arm portions 206-1 and 206-2 of the C-arm 206.

Since the C-arm 206 for holding the applicator 100 is slidable on the column 204 in the direction indicated by a double-headed arrow 212, the applicator 100 can be placed at a desirable height. In addition, as shown in FIG. 2, the applicator 10 can be inclined in the direction indicated by a double-headed arrow 210. Accordingly, the application can be approached to a desired location on a patient (not shown).

The applicator 100 is connected to electric equipment 300 over a cable 303 for feeding signals for driving the ultrasonic imaging probe 14. In addition, the applicator 100 is connected to water equipment 400 through three pipes 402 for supply and discharge of water and air. The cable 303 and pipes 402 can be disconnected by means of a connector 500 mounted on the C-arm 206. The connector 500 comprises a plug portion 500-1 for connection with shorter pipes (denoted by 40 and 42 in FIG. 4) extending from the applicator 100, and a socket portion 500-2 secured to the C-arm 206. The plug portion 500-1 is removable from the socket portion 500-2. Namely, by disconnection of the connector 500, a probe unit 600 comprising a probe rod 30 and shorter cables and pipes 303 and 402 can be separated from the applicator 100 and the hand-type holding apparatus 200. It is possible to prepare a number of probe units 600 having different frequency characteristics for tomographic imaging, and to use a suitable one of the units 600 in accordance with a region-of-interest. As a result, optimum tomographic imaging can be carried out, and reliable medial treatment can be performed.

Figure 4:
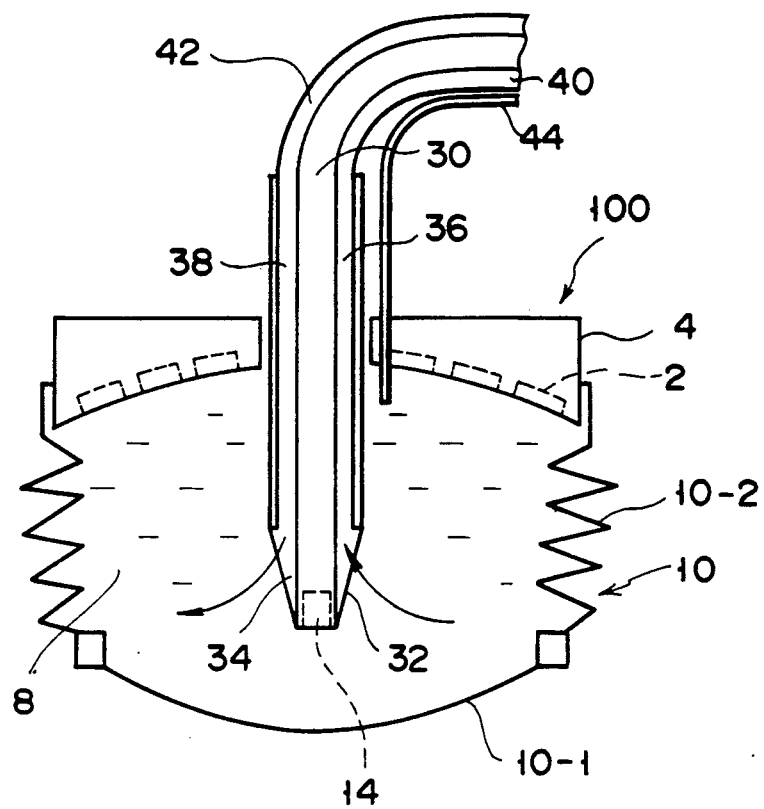
FIG. 4 is a cross-sectional view schematically showing an important portion (applicator) in the same embodiment.
Figure 5:
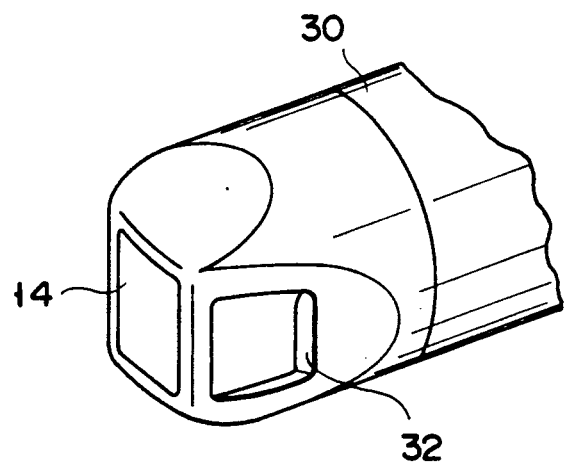
FIG. 5 is a perspective view showing an end portion of a probe rod in the same embodiment.
Figure 6:
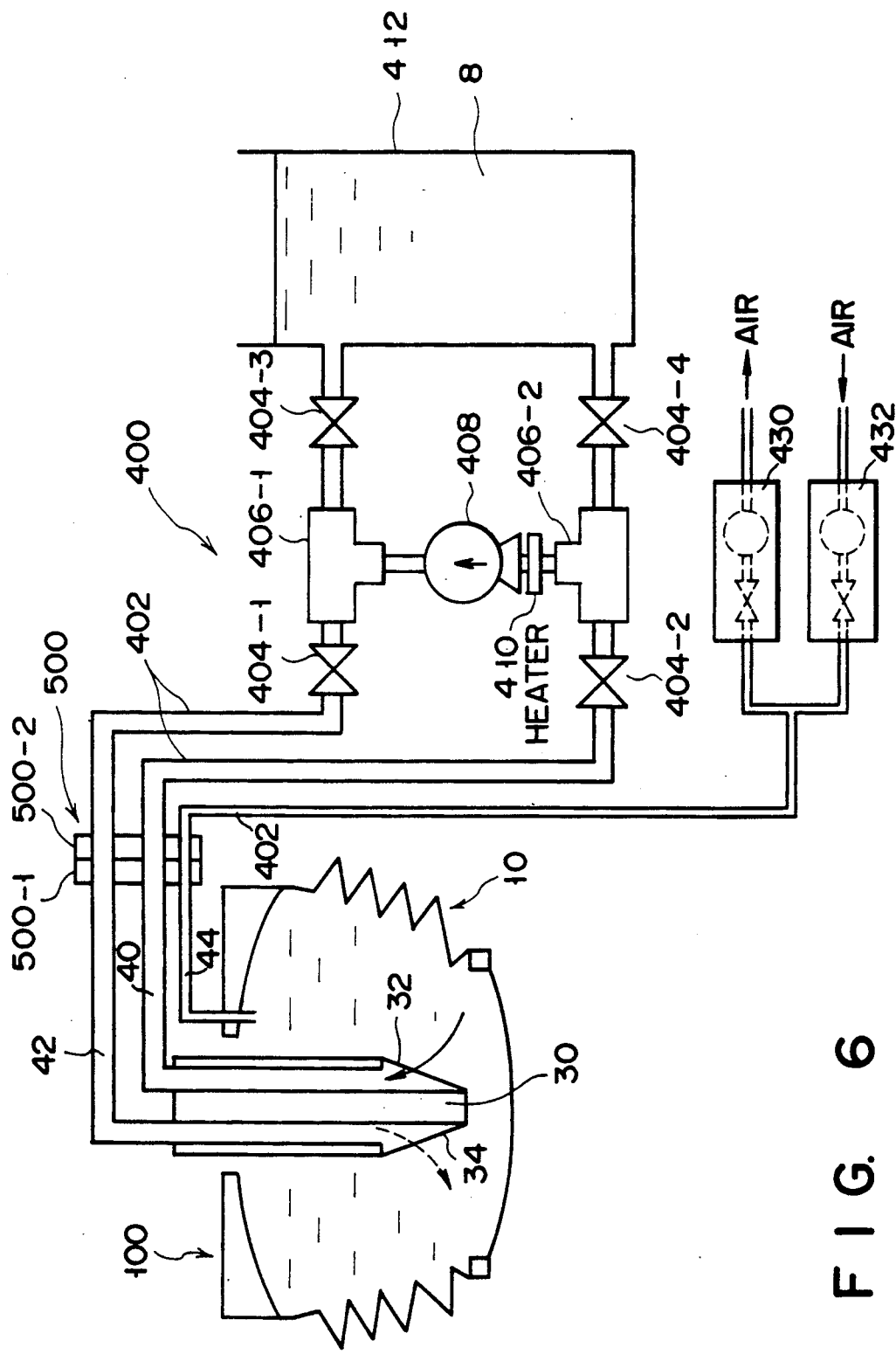
FIG. 6 shows an example of arrangement of pipes for connecting the applicator and water equipment in the same embodiment.

Referring to FIGS. 4 and 6, the applicator 100 and the probe rod 30 will now be described in detail. In the applicator 100, a holder 4 having a concave surface is provided with ultrasonic transducers 2 serving as an irradiation device, and a bag 10 containing water 8. The bag member 10 consists of a flexible water bag (diaphragm) 10-1 and a bellows 10-2.

Since the holder 4 has a concave surface, the medical treatment ultrasonic waves (pulse waves or continuous waves) emitted from the ultrasonic transducers 2 can be focused at a focal point determined by the shape of the concave surface of the holder 4. The holder 4 has a through-hole at its central portion. The probe rod 30 is inserted into the through-hole of the holder 4 and arranged vertically movable in the bag member 10. Otherwise, the holder 4 may have a through-hole positioned elsewhere to receive the probe. The bag member 10 is put in close contact with the patient 12. The size of the bag member 10 can be varied by increasing/decreasing the amount of water 8 contained in the bag member 10. Namely, the medical treatment ultrasonic waves can be focused at a desired point in the patient 12, by varying the size of the bag member 10 put in close contact with the patient 12.

An ultrasonic probe 14 is provided at an end portion of the probe rod 30. Water ports 32 and 34 are provided in the vicinity of the ultrasonic probe 14. For example, the port 32 serves as a suction port, and the port 34 serves as a supply port. Water passages 36 and 38 extend along the longitudinal axis of the probe rod 30. The passages 36 and 38 are connected at one end to the water ports 32 and 34 and connected at the other end, e.g. to first ends of the pipes 40 and 42. The second ends of the pipes 40 and 42 are connected to the plug portion 500-1 of the connector 500 shown in FIG. 2. A pipe 44, through which air is supplied to or discharged from the inside of the applicator 100, is arranged above the holder 4.

The passages 36 and 38 extending along the longitudinal axis of the probe rod 30 may be replaced with two pipes extending similarly along the longitudinal axis of the probe rod 30. According to an example shown in FIG. 5, the water ports 32 and 34 are formed not at the wave transmitting/receiving face (the end portion of the probe rod 30) of the ultrasonic probe 14, but a little above the end portion of the ultrasonic probe 14. Of course, the water ports 32 and 34 may be formed at the the wave transmitting/receiving face (the end portion of the probe rod 30).

Referring to FIG. 6, the water equipment connected to the socket portion 500-2 of the connector 500 will now be described. The water equipment 400 comprises pipes 402 for interconnecting various valves (described later), an electromagnetic valve (MV2) 404-1, an electromagnetic valve (MV2) 404-2, an electromagnetic valve (MV3) 404-3, an electromagnetic valve (MV4) 404-4, a three-way valve (TV1) 406-1, a three-way valve (TV2) 406-2, a pump (P) 408, a temperature controller (H) 410, a water tank 412, a vacuum pump (VP) 430 for sucking air from the applicator 100, and a compression pump (CP) 432 for supplying air into the applicator 100. It is desirable that the temperature controller (H) 410 be arranged midway along the passage for supplying, circulating and discharging water, as shown in FIG. 6.

Figure 7:
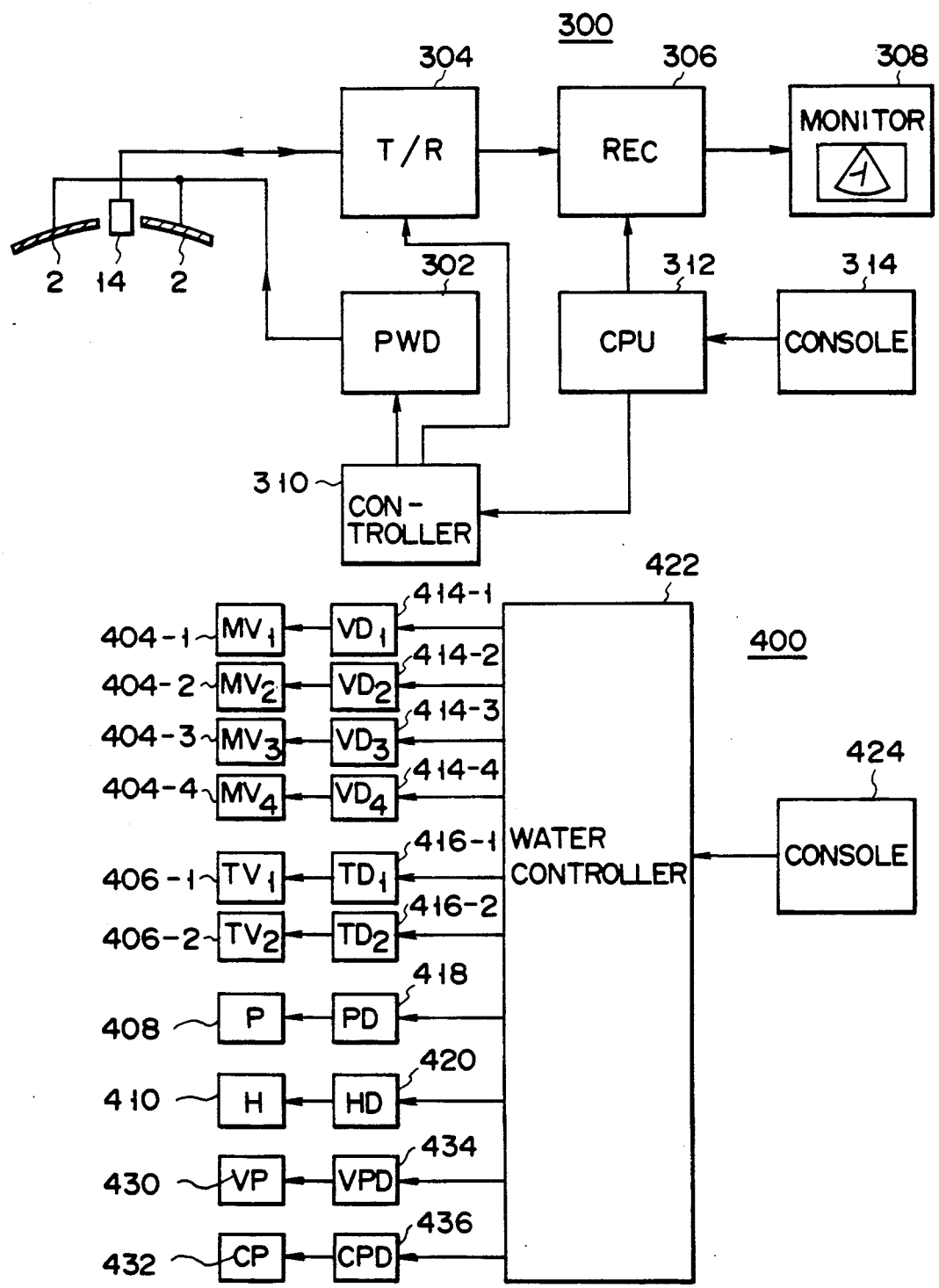
FIG. 7 is a block diagram showing an electric circuit in the case where the embodiment shown in FIG. 2 has been applied to an ultrasonic shock wave lithotrity apparatus.

FIG. 7 illustrates an electric circuit of the electric equipment 300 and the water equipment 400. The electric circuit of the electric equipment 300 comprises a pulse wave driver (PWD) 302 for pulse-driving the ultrasonic transducers 2, a transmitter/receiver 304 for enabling the ultrasonic probe 14 to transmit/receive ultrasonic waves for tomographic imaging, a reconstruction device (REC) 306 for producing a tomogram on the basis of a signal output from the transmitter/receiver 304, a monitor 308 for displaying the tomogram produced by the reconstruction device 306, a controller 310 for controlling the transmitter/receiver 304 and the pulsewave driver 302, a CPU 312 for controlling the controller 310, and a console 314 for supplying a command to the CPU 312.

In the above embodiment, the ultrasonic transducers 2 are driven by high-voltage pulses applied from the PWD 302, thereby generating shock waves for lithotrity. However, the ultrasonic transducers 2 may be driven by a driver (not shown) with a low power, so that envelope data is obtained from the received echo. The envelope data contributes greatly to enhance the precision of coincidence between the region-of-interest and the focal point of shock waves for lithotrity.

The electric circuit of the water equipment 400 comprises valve drivers (VD1, VD2, VD3 an VD4) 414-1, 14-2, 414-3 and 414-4, three-way valve drivers (TD1 and TD2) 416-1 and 416-2, a pump driver (PD) 418, a temperature control driver (HD) 420, a vacuum pump driver (VPD) 434 for driving the vacuum pump 430, a compression pump driver (CPD) 436 for driving the compression pump 432, a water controller 422 for controlling these drivers, and a console 424 for supplying commands to the water controller 422.

The operation of the above-described embodiment will now be described with reference to FIGS. 8A to 8C, FIGS. 9A to 9B, and FIGS. 10A and 10B.

Figure 8A:
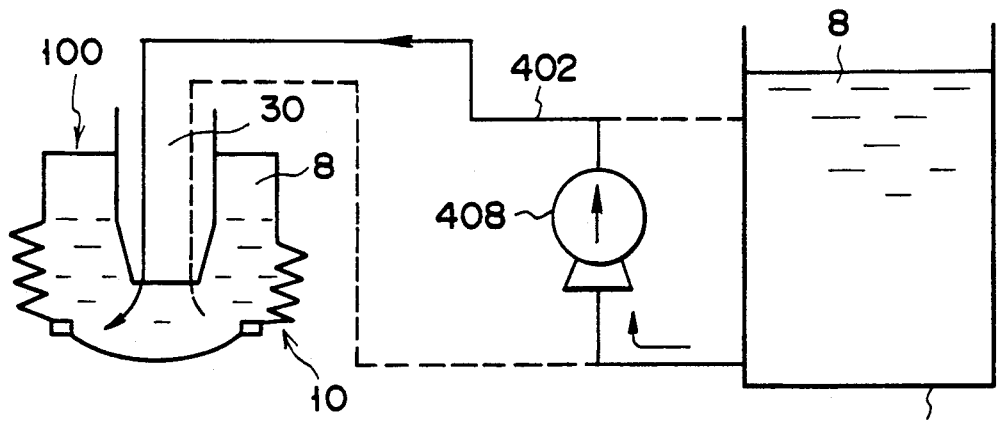

FIG. 8A illustrates a water supply mode of the acoustic wave therapy apparatus. In the water supply mode, the electromagnetic valves 404-1 and 404-4 are opened and the electromagnetic valves 404-2 and 404-3 are closed by the operation of the water controller 422. Thus, the pump 408 is operated. The water 8 is supplied from the tank 412 into the applicator 100 through the pipes 402 and 42, thereby swelling the bag member 10.

Figure 8B:
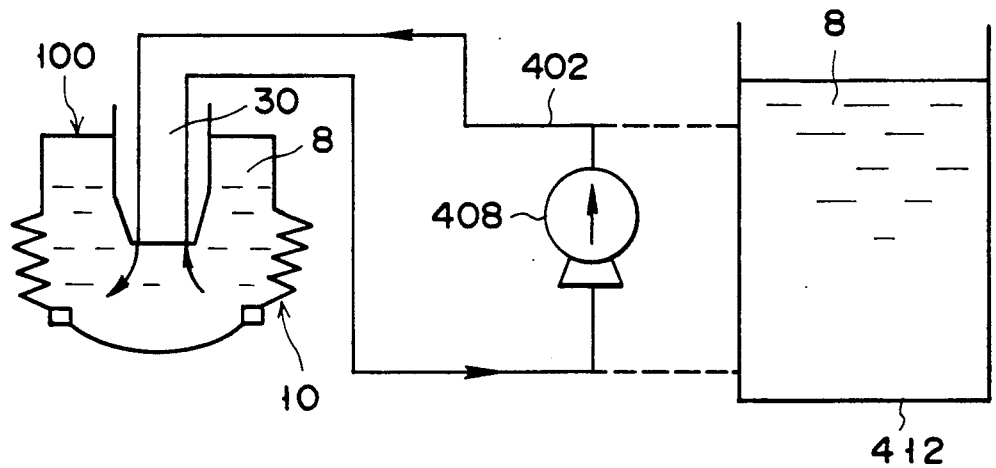

FIGS. 6 and 8B illustrate a water circulation mode of the apparatus. In the water circulation mode, the electromagnetic valves 404-3 and 404-4 are closed and the electromagnetic valves 404-1 and 404-2 are opened by the operation of the water controller 422. Thus, the pump 408 is operated. The water 8 in the applicator 100 can be circulated through the pipes 402, 40 and 42. In this case, the water 8 in the applicator 100 can be cooled or heated by lowering or raising the temperature via the temperature controller (HD) 410 and the driver 420.

Figure 8C:
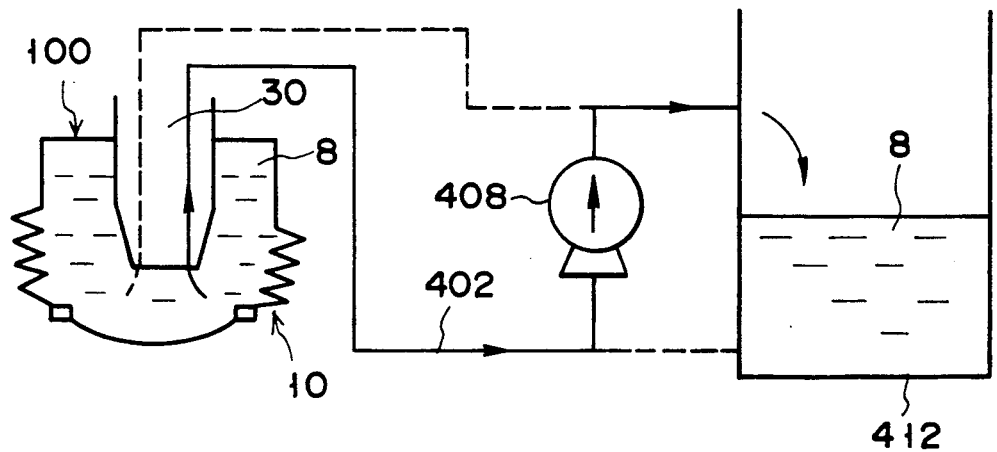

FIG. 8C illustrates a water discharge mode of the apparatus. In the water discharge mode, the electromagnetic valves 404-1 and 404-4 are closed and the electromagnetic valves 404-2 and 404-3 are opened by the operation of the water controller 422. Thus, the pump 408 is operated. The water 8 is discharged from the applicator 100 to the tank 412 through the pipes 402 and 40. Thus, the bag member 10 is contracted.

According to this apparatus, the water 8 in the bag member 10 can be discharged almost completely, by virtue of the water ports 32 and 34 formed at the probe rod 30. Even if a small amount of water 8 remains on the bottom of the bag member 10, the ultrasonic probe 14 is not immersed in the water 8, and the characteristics of the probe 14 are not degraded. Of course, if the water ports 32 and 34 are formed at the lowest part of the probe rod 30, the water 8 can be discharged completely. This makes easier the cleaning of the inside of the applicator 100 and the replacement of the bag member 10. In the water supply mode, water circulation mode, and water discharge mode, the vacuum pump 430 or the compression pump 432 is operated suitably. In the water supply mode, the amount of air, which corresponds to the amount of water to be supplied, is discharged.

In the water discharge mode, the amount of air, which corresponds to the amount of water to be discharge, is supplied. Thus, the bag member 10 is prevented from deformation, while the length of the bellows 10-2 is kept unchanged In addition, it is easy to discharge the water 8 from the applicator 100 completely, and to replace the bag member 10.

Figure 9A:
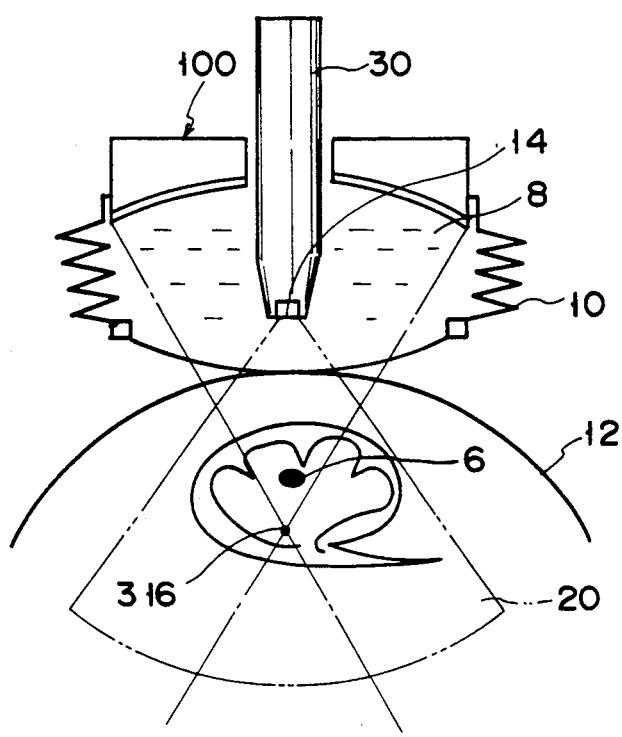
Figure 9B:
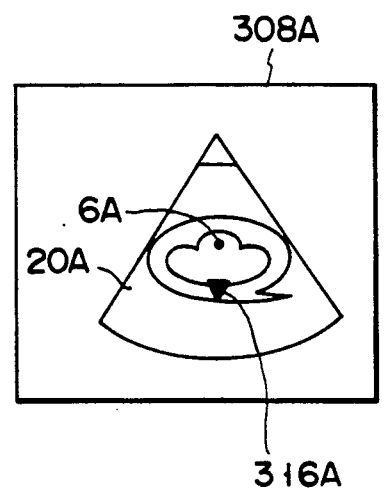
Figure 10A:
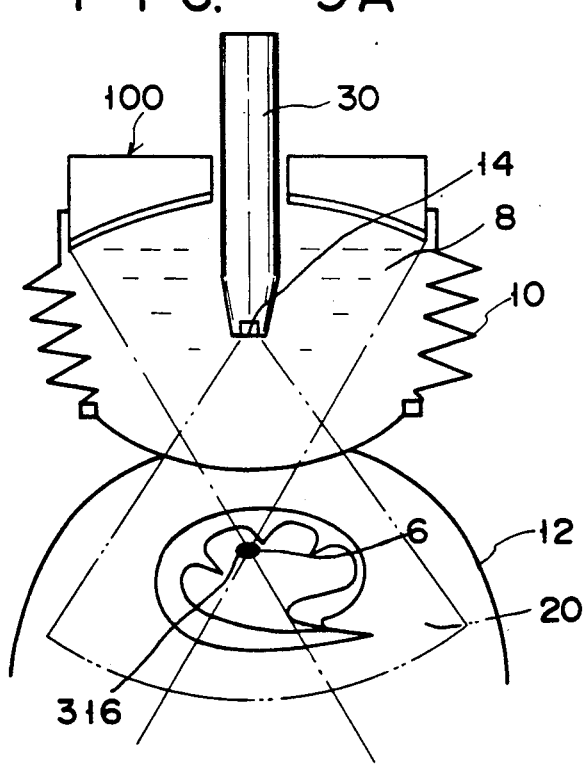
Figure 10B:
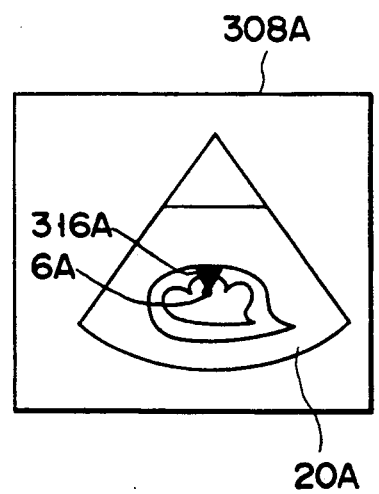

By virtue of the above-described water supply mode and the water discharge mode, the focal point of the medical treatment acoustic waves can be made to coincide with a region-of-interest (ROI) in the patient 12. More specifically, FIG. 9A shows the case where the applicator 100 is put on the patient 12 but the amount of water 8 in the applicator 100 is insufficient. In this case, as shown in FIG. 9B, a marker "▼" 316A representing a focal point 316 departs from an image 6A representing the ROI 6, in an image 20A shown on a screen 308A of the monitor 308. In order to make the focal paint 316 coincide with the ROI 6, the water 8 is supplied into the bag member 10 of the applicator 100 in the water supply mode. As a result, as shown in FIG. 10A, the focal point 316 coincides with the ROI 6. On the screen 308A shown in FIG. 10B, too, it is confirmed that the marker " " 316A representing the focal point 316 coincides with the image 6A representing the ROI 6.

FIG. 11 shows a case where the acoustic wave therapy apparatus shown in FIGS. 2 to 6 is employed as an ultrasonic continuous wave hyperthermic therapy apparatus. In this case, the pulse wave driver (PWD) 302 is replaced with a continuous wave driver (CWD) 318.

Figure 12:
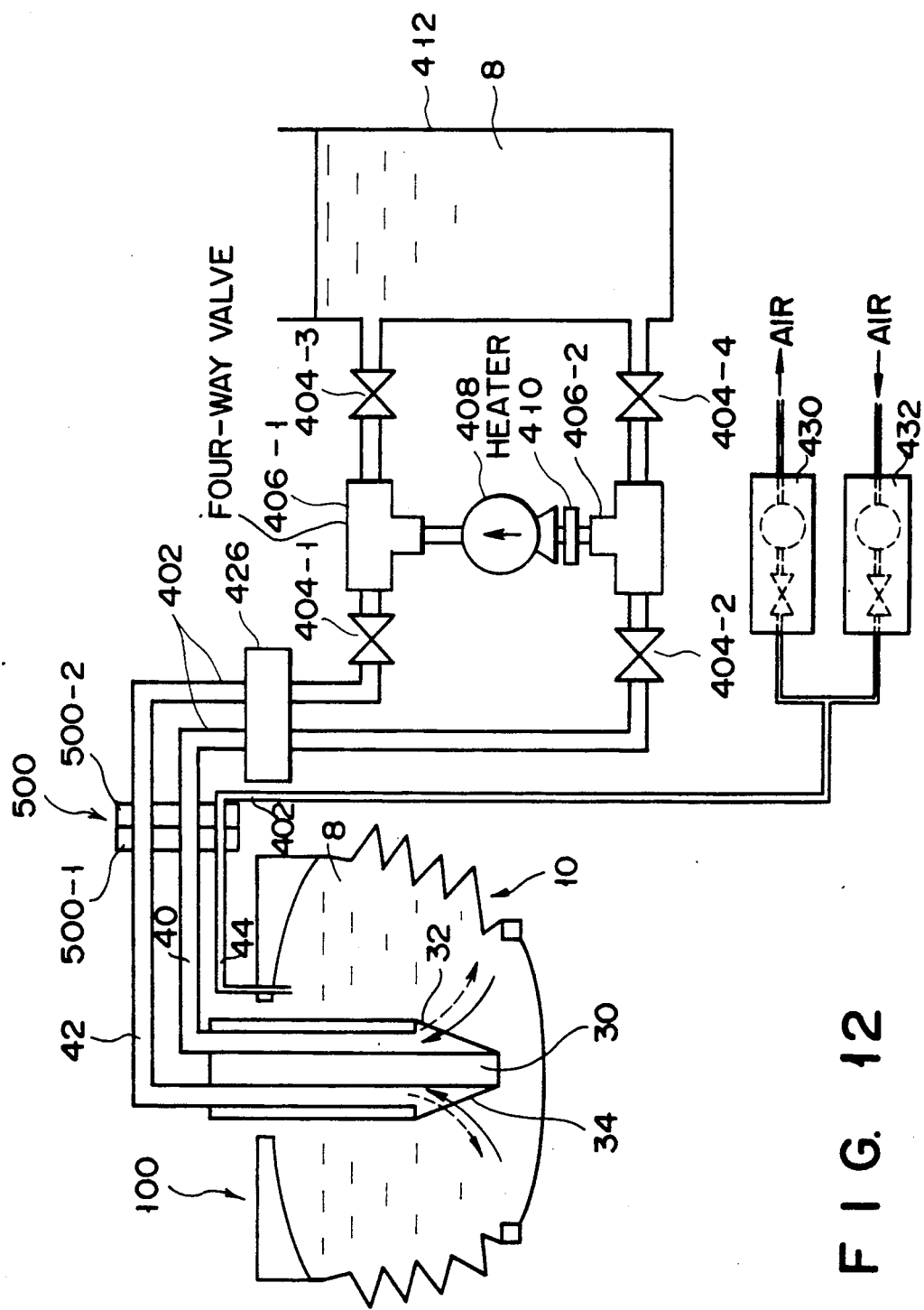
FIG. 12 shows another example of arrangement of pipes for connecting the applicator shown in FIG. 4 and water equipment.

Referring to FIG. 12, a description will now be given of a modification of the water equipment of the acoustic wave therapy apparatus shown in FIGS. 2 to 5. In this modification, a four-way valve 426 is arranged midway along the pipes 402, and the four-way valve 426 is controlled by a driver (not shown) and the water controller 422. By virtue of this structure, it becomes possible to use the water ports 32 and 34 and passages 40 and 42 simultaneously for supplying water, and also to use them simultaneously for discharging water. Thus, the water supply/discharge performance can be doubly enhanced.

Figure 13:
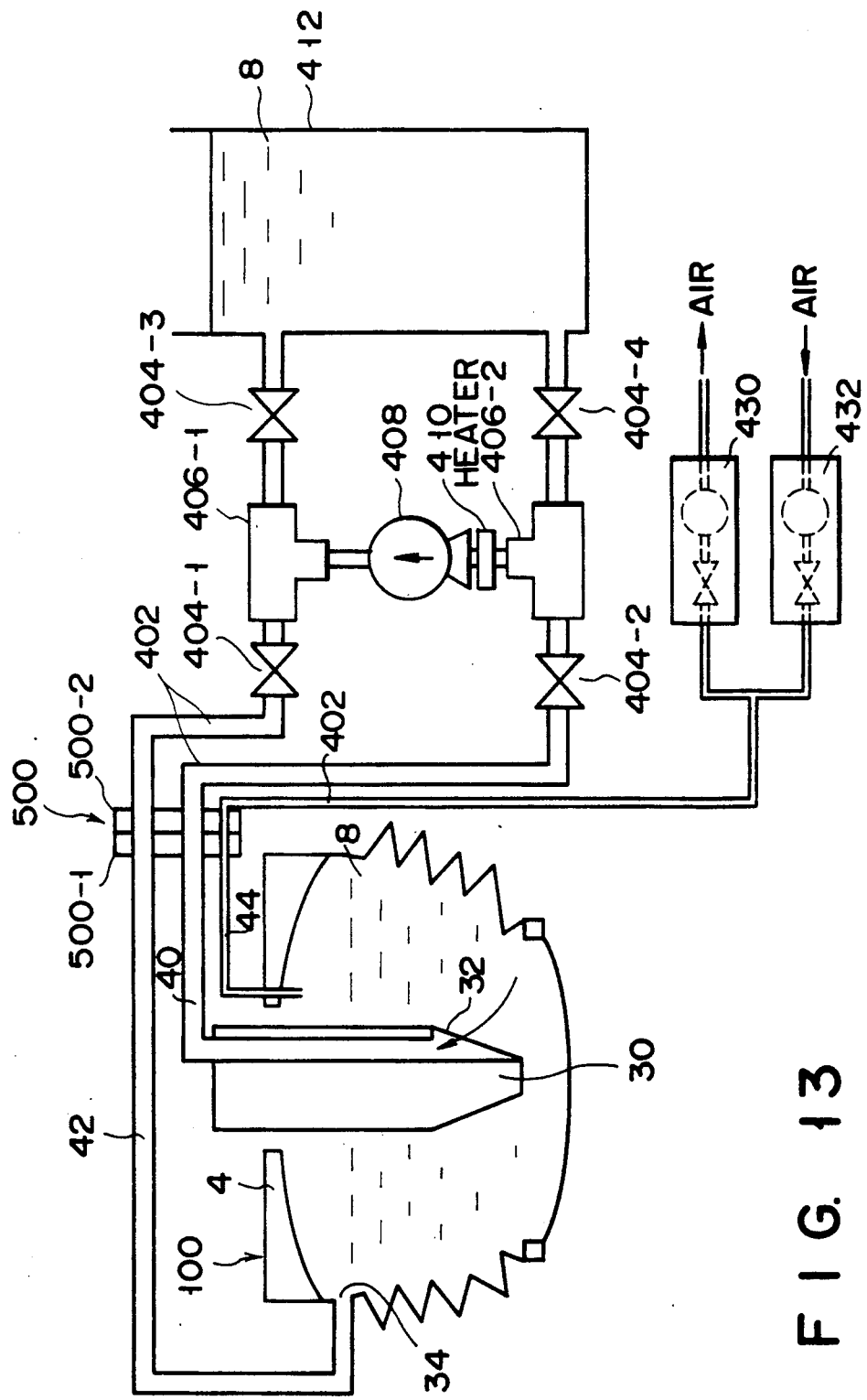
FIG. 13 shows an example of arrangement of pipes for connecting an applicator, different from that shown in FIG. 4, and water equipment.

Referring to FIG. 13, a description will now be given of a modification of the applicator 100 of the acoustic wave therapy apparatus shown in FIGS. 2 to 6. In this applicator, one water port 32 is formed at the probe rod 30, and the other water port 34 is formed at the holder 4. This makes the structure of the probe rod 30 simpler.

The cables 303 and pipes 402 may be arranged in order by means of a simple holder, without using the connector 500 which allows the disconnection of the cables 303 and pipes 402.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An acoustic wave therapy apparatus comprising:
   a holder having a concave surface at least on one side thereof, and also having a through-hole;
   acoustic wave generating means, provided on said one side of said holder, for generating acoustic waves for medical treatment;
   a bag member arranged on said one side of the holder and adapted to be put in contact with the surface of a subject, and containing an acoustic wave propagation medium;
   a vertically adjustable rod member inserted into said through-hole of the holder in said bag member; and
   an ultrasonic probe for ultrasonic wave tomographic imaging provided at an end portion of the rod member,
   wherein said rod member has at least one opening, a pipe member connected to the opening, and a supply and discharge means for supplying and discharging the acoustic wave propagation medium into or from said bag member through said pipe member; the bag member being variable in size to accommodate said supplied and discharged medium.

2. The apparatus according to claim 1, wherein said acoustic wave generating means is adapted to generate high-intensity pulse waves for lithotrity.

3. The apparatus according to claim 1, wherein said acoustic wave generating means is adapted to generate high-intensity continuous waves for hyperthermic therapy.

4. The apparatus according to claim 1, wherein said acoustic wave propagation medium is water.

5. The apparatus according to claim 1, wherein said supply and discharge means includes means for heating the medium.

6. The apparatus according to claim 1, wherein said supply and discharge means includes circulation means for circulating the acoustic wave propagation medium in the bag member by supplying and discharging the acoustic wave propagation medium into or from the bag member.

7. The apparatus according to claim 1, wherein said supply and discharge means includes heating means, provided midway along the pipe, for heating the acoustic wave propagation medium.

8. The apparatus according to claim 1, wherein said supply and discharge means includes an air supply and discharge member, for supplying and discharging air into and from the inside of the bag member.

9. The apparatus according to claim 1, wherein said holder is held by a holding apparatus.

10. The apparatus according to claim 9, wherein said hand-type holding apparatus comprises a base set on the floor, a column vertically arranged on the base, a C-arm mounted slidably on the column, and a holding mechanism provided on the C-arm for holding the holder.

11. The apparatus according to claim 10, wherein said holding mechanism comprises a ball-and-socket joint mechanism.

12. The apparatus according to claim 10, wherein a connector is secured on said C-arm, for connecting and disconnecting at least said pipe.

13. An acoustic wave therapy apparatus comprising:
a holder having a concave surface at least on one side thereof, and also having a through-hole;
acoustic wave generating means, provided on said one side of said holder, for generating acoustic waves for medical treatment;
a bag member arranged on said one side of the holder and adapted to be put in contact with the surface of a subject, and containing an acoustic wave propagation medium;
a vertically adjustable rod member inserted into said through-hole of the holder in said bag member; and
an ultrasonic probe for ultrasonic wave tomographic imaging provided at an end portion of the rod member,
wherein said rod member has a plurality of openings, a plurality of pipes connected to the openings, and supply and discharge means for supplying and discharging the acoustic wave propagation medium into or from said bag member through the pipes, the bag being variable in size to accommodate said supplied and discharged medium.

14. The apparatus according to claim 13, wherein said acoustic wave generating means is adapted to generate high-intensity pulse waves for lithotrity.

15. The apparatus according to claim 13, wherein said acoustic wave generating means is adapted to generate high-intensity continuous waves for hyperthermic therapy.

16. The apparatus according to claim 13, wherein said acoustic wave propagation medium is water.

17. The apparatus according to claim 13, wherein said supply and discharge means includes fluid equipment connected to said plurality of pipes.

18. The apparatus according to claim 17, wherein said fluid equipment includes an air supply and discharge member, for supplying and discharging air into and from the inside of the bag member.

19. The apparatus according to claim 17, wherein said fluid equipment includes circulation means for circulating the acoustic wave propagation medium in the bag by a member supply and discharge operation.

20. The apparatus according to claim 17, wherein said fluid equipment includes a temperature controller provided midway along the pipes, for heating and cooling the acoustic wave propagation medium.

21. The apparatus according to claim 13, wherein said holder is held by a holding apparatus, and said holding apparatus comprises a base set on the floor, a column vertically arranged on the base, a C-arm mounted slidably on the column, and a holding mechanism provided on the C-arm for holding the holder by means of a ball-and-socket joint mechanism.

22. The apparatus according to claim 13, wherein a connector is secured on a C-arm, for connecting and disconnecting at least said pipes.

23. An acoustic wave therapy apparatus comprising:
a holder having a concave surface at least on one side thereof, and also having a through-hole;
acoustic wave generating means, provided on said one side of said holder, for generating acoustic waves for medical treatment;
a bag member of variable size arranged on said one side of the holder and adapted to be put in contact with the surface of a subject, and containing an acoustic wave propagation medium;
a vertically adjustable rod member inserted into said through-hole of the holder in said bag member; and
an ultrasonic probe for ultrasonic wave tomographic imaging provided at an end portion of the rod member,
wherein said rod member has at least one opening at its one end, a pipe is connected to the opening, and fluid equipment means connected to said pipe for supplying and discharging the acoustic wave propagation medium into or from said bag member, the bag being variable in size to accommodate said supplied and discharged medium,
said holder being held by a holding apparatus, said holding apparatus comprises a base set on the floor, a column vertically arranged on the base, a C-arm mounted slidably on the column, and a holding mechanism provided on the C-arm for holding the holder, and
a connector is provided on the C-arm, for connecting and disconnecting at least said pipe.

* * * * *